United States Patent [19]

Reiner et al.

[11] 4,322,398

[45] Mar. 30, 1982

[54] IMPLANTABLE DRUG DEPOT AND PROCESS FOR THE PRODUCTION THEREOF

[75] Inventors: Roland Reiner, Eishborn; Wolfgang Kißing, Eschwege; Helga Döring, Cologne; Kari Köster-Lösche, Usingen; Helmut Heide, Kelkheim, all of Fed. Rep. of Germany

[73] Assignee: Battelle Institut e.V., Frankfurt am Main, Fed. Rep. of Germany

[21] Appl. No.: 13,068

[22] Filed: Feb. 21, 1979

[30] Foreign Application Priority Data

Feb. 20, 1978 [DE] Fed. Rep. of Germany ....... 2807132

[51] Int. Cl.$^3$ .................. A61K 9/26; A61K 9/32; A61L 15/03
[52] U.S. Cl. ......................... 424/19; 3/1.9; 128/260; 424/81
[58] Field of Search ................. 424/19–22, 424/28, 81; 526/298; 260/42.53; 3/1.9; 128/260

[56] References Cited

U.S. PATENT DOCUMENTS

| 2,967,802 | 1/1961 | Towey et al. | 167/78 |
|---|---|---|---|
| 3,443,261 | 5/1969 | Battista et al. | 3/1 |
| 3,483,870 | 12/1969 | Coover et al. | 424/81 |
| 3,527,841 | 9/1970 | Wicker et al. | 526/298 |
| 3,559,652 | 2/1971 | Banitt et al. | 526/298 |
| 3,564,078 | 2/1971 | Wicker et al. | 424/81 |
| 3,591,676 | 7/1971 | Hawkins et al. | 424/81 |
| 3,608,071 | 9/1968 | Relyveld | 424/88 |
| 3,713,860 | 1/1973 | Aukern | 117/8.5 |
| 3,759,264 | 9/1973 | Coover et al. | 526/298 |
| 3,767,437 | 10/1973 | Cruz | 106/161 |
| 3,787,900 | 9/1971 | McGee | 3/1 |
| 3,790,507 | 1/1974 | Hodosh | 260/2.5 R |
| 3,808,606 | 5/1974 | Tronzo | 3/1 |
| 3,855,638 | 12/1974 | Pilliar | 3/1 |
| 3,867,190 | 2/1975 | Schmitt et al. | 117/138.8 A |
| 3,887,699 | 6/1975 | Yolles | 424/19 |
| 3,896,077 | 7/1975 | Leonard et al. | 526/298 |
| 3,918,100 | 11/1975 | Shaw et al. | 3/1.9 |
| 3,925,545 | 12/1975 | Relyveld | 424/92 |
| 3,976,071 | 8/1976 | Sadek | 128/260 |
| 3,991,766 | 11/1976 | Schmitt | 128/335.5 |
| 4,016,252 | 4/1977 | Relyveld | 424/88 |
| 4,032,993 | 7/1977 | Conquard | 3/1 |
| 4,051,598 | 10/1977 | Sneer | 32/10 A |
| 4,093,576 | 6/1978 | deWijn | 424/81 X |
| 4,141,864 | 2/1979 | Rijke et al. | 260/42.53 |
| 4,156,943 | 6/1979 | Collier | 3/1.9 |
| 4,177,524 | 6/1979 | Grell et al. | 3/1.9 |
| 4,191,740 | 3/1980 | Heusser et al. | 424/81 X |
| 4,191,743 | 3/1980 | Klemm et al. | 424/81 X |
| 4,195,366 | 4/1980 | Jarcho et al. | 3/1.9 |
| 4,206,516 | 6/1980 | Pilliar | 3/1.9 |
| 4,239,113 | 12/1980 | Gross et al. | 424/81 X |

FOREIGN PATENT DOCUMENTS

| 2242867 | 2/1974 | Fed. Rep. of Germany . |
|---|---|---|
| 2620890 | 11/1977 | Fed. Rep. of Germany . |
| 2620891 | 11/1977 | Fed. Rep. of Germany . |
| 2620907 | 11/1977 | Fed. Rep. of Germany . |
| 2807132 | 8/1979 | Fed. Rep. of Germany . |
| 2827529 | 1/1980 | Fed. Rep. of Germany . |
| 1541793 | 3/1979 | United Kingdom . |

OTHER PUBLICATIONS

C.A. 89:12193r (1978), 88:177250z, 158414q, 459y (1978), 87:28970m, 177981t (1977), 86:34341v (1977).
C.A. 83:1523040, 65343x (1975), 82:103113m, 103114n, 47710g (1975), 80:112682q (1974), 75:112843g (1971).
C.A. 67:72296g (1967), 68:76778j, 27977q, 11587b, 11588c (1968), 69:95984k (1968), 72:101487f (1970).
C.A. 71:81975n (1969), 77:102916k (1972), 81:58167y (1974).
C.A. 89:144878c (1978).
C.A. 93:138032p, 210315c (1980), 92:203609c, 82460m, 169090q, 135160x, 116473k (1980).
C.A. 91:198960h, 181401d, 208991k (1979), 90:174702d (1979), 89:152615c (1978).
"Resorbierbare keramische Werkstoffe fur den Knochenersatz", Biomedizinische Technik, vol. 20, May 1975, p. 115 ff.
"Neuere Werkstoffe in der medizinischen Technik", Chemie-Ingenieur-Technik, No. 8, 1975, pp. 327 to 333.
Chemical Abstracts, (Lautenschlager et al.), vol. 86, 34247b.
Chemical Abstracts, (Gross et al.), vol. 86, 47297t.
Chemical Abstracts, (Nelson et al.), vol. 88, 15841q.
Chemical Abstracts, (Rosenthal et al.), vol. 86, 34234.
Chemical Abstracts, (Rijke et al.), vol. 87, 28970m.
Chemical Abstracts, (Hubbard et al.), vol. 82, 103113m.
Chemical Abstracts, (Relyveld), vol. 71, 11401y.
Koster, Kari et al., Langenbecks Archiv. fur Chirurgie, 341, 77–86, (1976).
Chemical Abstracts, (Relyveld), vol. 80, 112611h.

Primary Examiner—Shep K. Rose
Attorney, Agent, or Firm—Fisher, Christen & Sabol

[57] ABSTRACT

An implantable drug depot for the treatment of diseases of the bone or bone marrow. The depot consisting of a matrix in which at least one active ingredient is incorporated and contains at least one adjuvant agent to control the kinetics of the drug release. The matrix material consists of resorbable sintered calcium phosphate composed of CaO and $P_2O_5$ in a ratio between 5:1 and 2:1.

17 Claims, No Drawings

IMPLANTABLE DRUG DEPOT AND PROCESS FOR THE PRODUCTION THEREOF

BACKGROUND OF THIS INVENTION

This is the same as application Ser. No. 13,233, filed on Feb. 21, 1979, now abandoned. This is related to application Ser. No. 796,164, filed on May 17, 1977, now U.S. Pat. No. 4,202,055, and to application Ser. No. 795,165, filed on May 12, 1977, now U.S. Pat. No. 4,192,021.

1. Field of This Invention

This invention relates to the field of implantable drug depots for the treatment of the diseases of the bone and bone marrow.

2. Prior Art

At the present depots made of methacrylate/acrylate copolymers, which contain active ingredients such as sulphonamides, antibiotics and others, are used to treat infectious bone diseases. However, these polymers are not biodegradable and must therefore be removed by surgery after treatment has been completed.

The use of resorbable calcium phosphates as bone substitute is known [Langenbecks, Archiv fur Chirurgie, 341, 77–86, (1976)]. Not only can these materials be completely resorbed in the body, they also have properties which have a positive effect on bone growth.

BROAD DESCRIPTION OF THIS INVENTION

An object of this invention is to provide an implantable drug depot for the treatment of the diseases of the bone and bone marrow which overcomes the disadvantages of the known drug depots (deposits). Another object of this invention is to provide an implantable drug depot which permits an effective and improved release of therapeutic agents over a longer period of time that the known depots. A further object of this invention is an implantable drug depot for which subsequent removal of the matrix is not necessary. A still further object of this invention is to provide a process for the production of such implantable drug depot. Other advantages and objects of this invention are set out herein or are obvious herefrom to one ordinarily skilled in the art.

The objects and advantages of this invention are achieved by the implantable drug depots and processes of this invention.

This invention solves the prior art problems in a technically advanced way, whereby the matrix material of the depot consists of resorbable, sintered calcium phosphates which are composed of CaO and $P_2O_5$ in a ratio of between 5:1 and 2:1, preferably 3:1, and the depot contains an adjuvant agent to control the kinetics of the drug release.

This invention concerns an implantable drug depot for the treatment of diseases of the bone and bone marrow, the depot consisting of a matrix in which an active ingredient is incorporated, and a process for the production of the depot. The drug depot is particularly suitable for use in the prevention and treatment of infectious diseases of the bone and the bone marrow, e.g., osteomyelitis.

The implantable drug depot of this invention for the treatment of diseases of the bone or bone marrow consists of a matrix in which at least one active ingredient is incorporated and which contains at least one adjuvant agent to control the kinetics of the drug release. The matrix material consists of resorbable sintered calcium phosphate composed of CaO and $P_2O_5$ in a ratio between 5:1 and 2:1.

The calcium phosphate matrix used in this invention is produced from calcium hydrogen phosphate and calcium carbonate by reaction sintering. By varying the conditions of synthesis either the low temperature modification ($\beta$-Whitlockit) or the high temperature modification ($\alpha$-Whitlockit) or combinations of both modifications with a calcium phosphate glass phase can be obtained. The relative amounts of these modifications in the total structure influence the resorption rate of the material. However, these amounts can be varied within broad limits depending on the desired duration of the active ingredient supply.

The calcium phosphate matrix is combined with the other components of the drug depot according to this invention either in porous, solid form or in powder form. The calcium phosphate powder preferably has a grain size of less than 200 $\mu$m, while the calcium phosphate solid body has a pore ratio of 10 to 25 percent. Control of the rate of release of the active ingredient is also possible by appropriate variation of the pore structure of the matrix.

The pharmaceutical depot according to this invention contains an adjuvant agent (or adjuvant agents) to control the kinetics of the drug release and, if necessary, to stabilize the matrix material. Stabilization of the matrix material is required in particular when calcium phosphate powder is used as the matrix.

Derivatives of the saturated or unsaturated aliphatic carboxylic acids having between 10 and 20, preferably 15 to 18, carbon atoms in an amount up to 25, preferably 5 to 20, weight percent, based on the total weight of the drug depot, can be used as adjuvant agents. For example, n-hexadecanoic acid, octadecanoic acid and oleic acid are suitable for this purpose. The derivatives of the carboxylic acids are mainly alkaline (alkali) metal salts, alkaline earth metal salts, aluminum salts and triglycerides, lipids or mixtures of the same. Sodium and calcium salts are most preferably used as the alkaline (metal) salts or earth alkaline (metal) salts, respectively. Neutral or non-neutral phospholipids, preferably lecithins, or glycolipids can be used as the lipids. Mixtures of these derivatives are also suitable. Mixtures of triglycerides having melting points between 20° and 150° C. with phospholipids, or mixtures of the above-mentioned calcium, aluminum or sodium salts of the carboxylic acids with lecithins are preferably used.

As used herein, alkaline metals includes sodium, lithium, potassium, cesium and rubidum. As used herein alkaline earth metals includes calcium, barium, berylium, magnesium and strontium.

Furthermore, the active ingredient to be incorporated in the matrix can be encapsulated with a film-forming, resorbable polymer by known methods. But it is also possible to add the monomer to the mixture of all the components of the depot, so that in this case, after carrying out the polymerization, the matrix material is also coated. Suitable polymers are, for example, polycyanoacrylates, polyglycolic acid derivatives and polylactic acid derivatives. Coating of the active ingredient or the mixture from the matrix material and the active ingredient also helps to control the rate of release of the active ingredient. This means, for example, that when the active ingredient has a high serum solubility, the rate of release is essentially reduced.

For the production of the drug depot according to this invention, a calcium phosphate powder having a grain size of less than 200 μm is mixed with the active ingredient(s). Then one or more of the adjuvant agents are added to obtain a paste-like mass. If necessary, the pasty mass can be pressed into tablets using heat.

If, however, a porous, solid body consisting of calcium phosphate is used, then it should have an appropriate pore ratio of 10 to 25 percent. First, the porous calcium phosphate bodies are impregnated with a solution of the active ingredient in a first solvent (A). In order to obtain the best possible precipitation of the active ingredient within the porous body, the first solvent (A) is not removed by evaporation, but is replaced by a second solvent (B), in which the active ingredient is not soluble but which is at least mixable with the first solvent (A) to a limited extent. The second solvent (B) can then be evaporated. If necessary, this impregnation process can be repeated several times. The introduction of the adjuvant agents into the calcium phosphate body also occurs by soaking of the body with a solution of the adjuvant agents in a third solvent (C), which again does not dissolve the active ingredient but can be mixed with the second solvent (B) at least to a limited extent. Finally, the third solvent (C) is removed by evaporation. With an active ingredient that is soluble in water, for example, dioxane, tetrahydrofurane, n-butanol or acetone, among others, can be used as the second solvent (B) and hexane can be used as the third solvent (C) for the adjuvant agents.

DETAILED DESCRIPTION OF THIS INVENTION

As used herein, all parts, percentages and ratios are on a weight basis unless otherwise stated or otherwise obvious herefrom to one ordinarily skilled in the art.

The following examples describe this invention, but this invention is not limited to such invention.

EXAMPLE 1

Production of the matrix:

(a) Calcium hydrogen phosphate and calcium carbonate in a finely dispersed form are homogeneously mixed and pressed into tablets. These tablets are then sintered for 3 hours at 1200° C. Tricalciumphosphate is formed in the low temperature modification (β-Whitlockit) according to the formula:

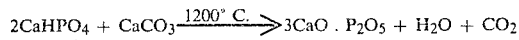

$$2CaHPO_4 + CaCO_3 \xrightarrow{1200° C.} 3CaO \cdot P_2O_5 + H_2O + CO_2$$

The tablets are reduced in size and ground to a powder having a grain size of less than 65 μm. This powder can already be used as the matrix material. Any shape, e.g., tablets or pellets, can be produced by pressing the dry powder, by slip casting or by plasticizing with water.

(b) By adding 30 weight percent of water to the powder produced as described above [in (a)], a pasty mass is formed which is pressed into a hole of a mold. After drying, the calcium phosphate bodies are pressed out of the mold and cylindrical pellets, 5 mm in diameter and 5 mm in height are obtained. The cylindrical pellets are sintered at a temperature of ca. 1500° C. In order to produce a ceramic bond the sinter temperature selected must be high enough that the low temperature modification (β-Whitlockit) is transformed into a high temperature modification (α-Whitlockit) and that a partial melt is also formed which cements the cyrstalline components together. By controlled, rapid cooling down of the sintering furnace to room temperature, the high temperature forms (α-Whitlockit and glass phase) are partially "frozen" so that only a part of these phases is transformed back into the low temperature form. In this manner the matrix is optimized with respect to its composition and microporosity and therefore also with respect to its biological properties, such as stability and resorbability.

Thus, the matrix bodies, for example, pellets, produced in the manner described above consist of α-and β-tricalcium phosphate and the glass phase. The material has a density of 2.47 g/cm$^3$ and a volume ratio of ca. 78.6 percent.

(c) The pellets produced as described above are ground to a powder and are screened by sieving to a grain size of 65 μm.

Examples 2 to 12 concern the production of the drug depot according to this invention.

EXAMPLE 2

10 calcium phosphate pellets which were produced according to the process of Example 1(b) are saturated in a solution of gentamicin sulphate in water. The mixture is then degassed by evacuating for 30 minutes. Finally, to precipitate the gentamicin sulphate in the porous pellet, dioxine is added. The calcium phosphate pellets are then put into a solution of lecithin in hexane and degassed by evacuation as described above.

The elution rate is determined using a matrix containing 3.2 mg of gentamicin sulphate. For this the drug depot is treated with 5 ml of a 0.066 molar phosphate buffer ($K_2HPO_4$/NaOH; pH 7.4) and left to stand at 37° C. The buffer is poured off at certain intervals and the quantity of gentamicin released against the bacillus subtilis is measured. After 24 hours, 21 percent of the gentamicin present has been elutriated.

EXAMPLE 3

10 calcium phosphate pellets, which were produced according to the process of Example 1(b) are saturated in a solution of quinacrine dihydrochloride in water. The active ingredient in the solution is precipitated in the pellets using dioxane, THF, n-butanol, ethyl acetate, acetone or diglycol dimethyl ether. The pellets are then put into a solution of lecithin in hexane and degassed by evacuation as described above in Example 2.

After 48 hours, the quantity of active ingredient released was 51 percent of the quantity contained in the calcium phosphate pellets.

EXAMPLE 4

8 grams of calcium phosphate powder produced according to the process of Example 1(c) are rubbed to a paste with 120 mg of chloroamphenicol and 200 g of hardened peanut oil at 50° C. The paste is pressed into 10 tablets. The release of active ingredient was 25 percent after 48 hours.

EXAMPLES 5 to 11

Calcium phosphate powder produced according to the process of Example 1(c), 12 mg of chloroamphenicol or gentamicin and an adjuvant agent (as specified in the table following the Examples) are mixed. Tablets of about 1 g with a diameter of 13 mm and a height of 3.5 mm are produced from the mixture at a pressure of 130 kp/cm². The rates of release of the active ingredients are summarized in the table following the Examples.

EXAMPLE 12

13 mg of chloroamphenicol and 850 mg of the calcium phosphate powder produced according to the process of Example 1(c) are mixed and then added to 120 mg of methyl cyanoacrylate. Tablets of about 1 g are produced from the mixture according to the process of Examples 5 to 11. The rate of release of the active ingredient is a total of 8.5 percent after 24 hours and a total of 10 percent after 42 hours.

If, however, chloroamphenicol and methyl cyanoacrylate are mixed together first, and the calcium phosphate powder is added after the beginning of the polymerization of the monomer, the rate of release of the active ingredient is a total of 18 percent after 24 hours and a total of 23 percent after 42 hours.

Examples 13 and 14 concern the production of a drug depot without the addition of adjuvant agents.

EXAMPLE 13

10 calcium phosphate pellets which were produced according to the process in Example 1(b) are put into 25 ml of a solution of quinacrine dihydrochloride in water at room temperature. The mixture is degassed by evacuation for 30 minutes. The solvent is then poured off and the pellets are put into 25 ml of tetrahydrofurane. The pellets are removed after several hours and dried until they achieve a constant weight. The impregnation process is repeated several times. With increasing concentrations of the active ingredient solution, a larger quantity of quinacrine can be introduced into the calcium phosphate pellets.

The release of active ingredient is determined using a calcium phosphate matrix containing 0.8 g of quinacrine dihydrochloride. It amounts to 92 percent after 48 hours.

EXAMPLE 14

The process in Example 13 is repeated except that chloroamphenicol is used as the active ingredient instead of quinacrine dihydrochloride, and alcohol is used as the solvent for the active ingredient. The release of active ingredient is 98 weight percent after 120 hours.

cium phosphate composed of CaO and $P_2O_5$ in a ratio between 5:1 and 2:1.

2. An implantable drug depot as claimed in claim 1 wherein said resorbable sintered calcium phosphate is composed of CaO and $P_2O_5$ in a ratio of 3 to 1.

3. An implantable drug depot as claimed in claim 1 wherein said matrix consists of pelleted calcium phosphate powder with a grain size of less than 200 $\mu$m or a microporous calcium phosphate body with a pore ratio of between 10 and 25 percent.

4. An implantable drug depot as claimed in claim 3 wherein one therapeutically active ingredient is present.

5. An implantable drug depot as claimed in claim 3 wherein said drug depot is in the form of a tablet.

6. An implantable drug depot as claimed in claim 3 wherein said therapeutically active ingredient is coated with said polymer of methyl cyanoacrylate.

7. An implantable drug depot as claimed in claim 3 wherein said matrix and said therapeutically active ingredient are coated with said polymer of methyl cyanoacrylate.

8. An implantable drug depot as claimed in claim 3 wherein said therapeutically active ingredient is chloroamphenicol.

9. An implantable drug depot for the treatment of diseases of the bone or bone marrow, consisting of a matrix in which at least one therapeutically active ingredient is incorporated and which contains a polycyanoacrylate, which helps control the rate of release of said therapeutically active ingredient, said matrix material consisting of resorbable sintered calcium phosphate composed of CaO and $P_2O_5$ in a ratio between 5:1 and 2:1.

10. An implantable drug depot as claimed in claim 9 wherein said resorbable sintered calcium phosphate is composed of CaO and $P_2O_5$ in a ratio of 3 to 1.

11. An implantable drug depot as claimed in claim 9 wherein said matrix consists of pelleted calcium phosphate powder with a grain size of less than 200 $\mu$m or a microporous calcium phosphate body with a pore ratio of between 10 and 25 percent.

12. An implantable drug depot as claimed in claim 11 wherein one therapeutically active ingredient is present.

13. An implantable drug depot as claimed in claim 11 wherein said drug depot is in the form of a tablet.

14. An implantable drug depot as claimed in claim 11

TABLE

| Example No. | Active Ingredient | Adjuvant % By Wt. Based On Total Weight | Accumulated Release Of Active Ingredient In Wt. % After The Enumerated Number Of Hours | | | | | | | | |
|---|---|---|---|---|---|---|---|---|---|---|---|
| | | | 12 | 24 | 48 | 70 | 96 | 120 | 148 | 172 | 288 |
| 5 | chloroamphenicol | — | 60 | 76 | 96 | 94 | 95 | 98 | — | — | — |
| 6 | chloroamphenicol | 10 Ca stearate | — | 13 | 19 | — | — | 31 | 35 | 38 | 50 |
| 7 | chloroamphenicol | 20 Al stearate | — | 9 | 17 | — | — | 32 | 38 | 43 | 60 |
| 8 | chloroamphenicol | 10 Al distearate | — | 17.5 | 28 | — | — | 45 | 52 | 56 | 71 |
| 9 | gentamicin | 20 Ca stearate | — | 9 | 14 | 18 | 22 | 24 | 27 | 29 | 35 |
| 10 | gentamicin | 10 Ca stearate | — | 21 | 29 | 34 | 36 | 38 | 39 | 40 | 41 |
| 11 | gentamicin | 20 Al palmite | — | 17 | 25 | 28 | 30 | 32 | 33 | 34 | 35 |

What is claimed is:

1. An implantable drug depot for the treatment of diseases of the bone or bone marrow, consisting of a matrix in which at least one therapeutically active ingredient is incorporated and which contains a polymer of methyl cyanoacrylate, which helps control the rate of release of said therapeutically active ingredient, said matrix material consisting of resorbable sintered calwherein said therapeutically active ingredient is coated with said polycyanoacrylate.

15. An implantable drug depot as claimed in claim 11 wherein said matrix and said therapeutically active ingredient are coated with said polycyanoacrylate.

16. An implantable drug depot as claimed in claim 11 wherein said therapeutically active ingredient is chloroamphenicol.

17. An implantable drug depot for the treatment of diseases of the bone or bone marrow, consisting of a matrix in which at least one therapeutically active ingredient is incorporated and which contains a polymer of methyl cyanoacrylate, which helps control the rate of release of said therapeutically active ingredient, said matrix material consisting of resorbable sintered calcium phosphate composed of CaO and $P_2O_5$ in a ratio between 5:1 and 2:1, said implantable drug depot being prepared by the process comprising (i) mixing said calcium phosphate, in powder form, and said therapeutically active ingredient, (ii) mixing said mixture (i) with said polymer of methyl cyanoacrylate, and forming said mixture (ii) into an implant.

* * * * *